US006187746B1

(12) United States Patent
Conrath et al.

(10) Patent No.: US 6,187,746 B1
(45) Date of Patent: Feb. 13, 2001

(54) PHARMACEUTICAL COMPOSITIONS BASED ON DALFOPRISTINE AND ON QUINUPRISTINE, AND PREPARATION THEREOF

(75) Inventors: Guillaume Conrath, Chatenay Malabry; Joël Vacus, Paris, both of (FR); Nicholas Paul Barker, Southborough, MA (US)

(73) Assignee: Rhone-Poulenc Rorer S.A., Antony (FR)

( * ) Notice: Under 35 U.S.C. 154(b), the term of this patent shall be extended for 0 days.

(21) Appl. No.: 09/210,938

(22) Filed: Dec. 15, 1998

Related U.S. Application Data
(60) Provisional application No. 60/095,692, filed on Aug. 7, 1998.

(30) Foreign Application Priority Data

Dec. 16, 1997 (FR) .................................. 97 15911

(51) Int. Cl.⁷ .................................. A61K 38/00
(52) U.S. Cl. .................................. 514/11
(58) Field of Search .................................. 514/11

(56) References Cited

U.S. PATENT DOCUMENTS 4,617,290 * 10/1986 Corbet et al. .................. 514/11

FOREIGN PATENT DOCUMENTS

248703 * 12/1987 (EP) .
2772272 * 6/1999 (FR) .

OTHER PUBLICATIONS

D. Low, "Quinupristin/Dalfopristin: Sprectrum of Activity, Pharmacokinetics, and Initial Chemical Experience, " Microbial Drug Resistance, 1(3):223–234, (1995).

E. Bernard et al., "Pharmacokinetics and Suction Blister Fluid Penetration of a Semisynthetic Injectable Streptogramin RP 59500 (RP 57669/RP 54476)", Eur. J. Clin. Microbiol. Infect. Dis. 13(9):768–771 (1994).

P. Simamora et al., "Studies in Phlebitis VIII: Evaluations of pH Solubilized Intravenous Dexverapamil Formulations", PDA J. of Pharm. Sci. & Tech. 50(2):123–128 (1996).

S. Gupta et al., "Parenteral Formulation Development of Renin Inhibitor Abbott–72517", J. of Pharm. Sci. & Tech. 48(2):86–91 (1994).

C. Chant et al., "Quinupristin/Dalfopristin (RP 59500): A New Streptogramin Antibiotic", The Annals of Pharm., 29(10):1022–1027 (1995).

* cited by examiner

*Primary Examiner*—Kevin E. Weddington
(74) *Attorney, Agent, or Firm*—Finnegan, Henderson, Farabow, Garrett & Dunner L.L.P.

(57) ABSTRACT

The present invention relates to injectable compositions containing a dalfopristine/quinupristine combination comprising an aqueous solution containing the dalfopristine/quinupristine combination and an additive intended to avoid or reduce the intolerance effects at the site of injection.

46 Claims, No Drawings

PHARMACEUTICAL COMPOSITIONS BASED ON DALFOPRISTINE AND ON QUINUPRISTINE, AND PREPARATION THEREOF

This application claims the benefit of priority of French Application No. 97 15911, filed Dec. 16, 1997, and U.S. Provisional Application No. 60/095,692, filed Aug. 7, 1998, and incorporates by reference those applications.

The present invention relates to injectable antibacterial pharmaceutical compositions intended for the parenteral administration of quinupristine and dalfopristine, without entailing side effects of intolerance at the site of injection.

European patent application EP 248,703 describes pristinamycin I derivatives of the general formula:

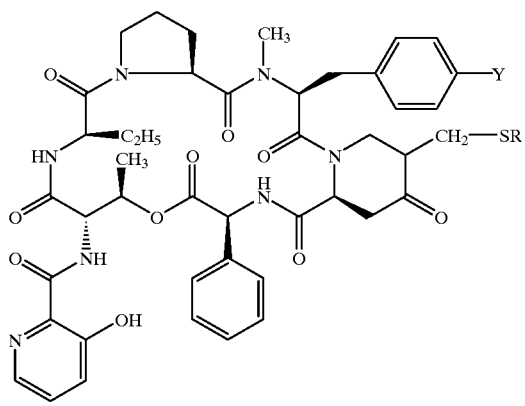

as well as their combination with pristinamycin II derivatives having the structure:

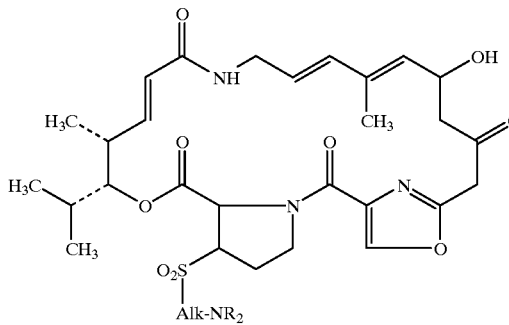

Quinupristine, a derivative of pristinamycin I, and dalfopristine, a derivative of pristinamycin II, are the components of Synercid®:

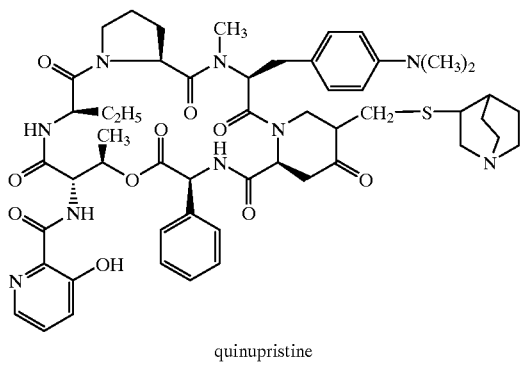

quinupristine

-continued dalfopristine

Synercid® (quinupristine/dalfopristine) is an injectable 30/70 combination whose antibacterial activity, in particular on vancomycin-resistant microorganisms is cited in many publications, e.g., The Annals of Pharmacotherapy, 29, 1022–1026 (1995); and Microbial Drug resistance, 1, 223–234 (1995).

Solubilization of the isolated components quinupristine or dalfopristine can be obtained in salt form. The preparation of stabilized pharmaceutical compositions comprising the quinupristine/dalfopristine combination proved to be very difficult and was finally achieved by adding at least stoichiometric amounts of methanesulphonic acid or hydrochloric acid, and were achieved at a pH within the range of from 3.5 to 5. These compositions also optionally contain a tonicity agent and/or other pharmaceutically acceptable adjuvants.

Attempts to prepare antibacterial pharmaceutical compositions comprising dalfopristine and quinupristine in the form of other salts have been unsuccessful due to the fact that one or both of the molecules was unstable either in solution or in lyophilized form.

The injection, in particular injection by infusion, of pharmaceutical compositions comprising the quinupristine/dalfopristine combination as described above entails venous intolerance effects localized in the region of the point of injection, which are manifested by inflammatory phenomena, phlebitis, allergic reactions or formation of oedemas which can go as far as to cause total interruption of the treatment. Such a situation is extremely troublesome since Synercid® (quinupristine/dalfopristine) currently proves to be among the only known clinical treatments for treating very serious infections caused by vancomycin-resistant microorganisms.

H. Yalkowsky et al., PDA Journal of Pharmaceutical Science & Technology, 50(2), 123–128 (1996) has described the study and improvement of phlebitis caused by the administration of the cardiovascular agent dexverapamil. However, this therapeutic agent has a chemical structure which is very different from those of the streptogramin family and there is furthermore no link in its physicochemical single properties.

S. L. Gupta et al., Journal of Pharmaceutical Science & Technology, 48(2), 86–91 (1994) has described the effects of various systems in order to overcome the pain and irritation during injection caused by the antihypertensive agent Abbott 72517, among which is the use of a buffer. Pharmaceutical formulations including a buffer are also there described. However, not only is this an isolated product, rather than two combined molecules each having their particular nature, but it is also not a chemically similar structure which would allow transposition with some reasonable chances of success.

Furthermore, it has not been possible to prepare stable pharmaceutical compositions of the quinupristine/dalfopristine combination with citric acid or acetic acid.

It has now been found, and this forms the subject of the present invention, that the use of an additive, combined with the injection of the antibacterial pharmaceutical composition comprising the quinupristine/dalfopristine combination, can reduce, or even eliminate entirely, the localized side effects entailed by this combination of active principles. This occurrence is surprising, given the very different nature of each of the molecules combined and the difficulties associated with the instability of certain salts of one or the other of these molecules, e.g., the appearance of many degradation impurities, as well as the poor solubility and the instability of these active principles at certain pH values.

Thus, the additive has a protective role with respect to the venous intolerance effects entailed by the injection of the quinupristine/dalfopristine combination.

Formulations of the quinupristine/dalfopristine combination exist in liquid, lyophilized or frozen form.

The lyophilized formulations can be taken up, at the time of use, in water for injectable preparations (water fip) or in any compatible injectable medium, in particular in media such as glucose solutions, for example, an aqueous 5% glucose solution, or without any limitation being implied, with dextran solutions, polyvinylpyrrolidone solutions or polysorbate 80 solutions. According to a preferred method, the formulations are taken up in solution by passing via a concentrated solution of 50 to 250 mg/ml, preferably of about 100 mg/ml, referred to hereinbelow as the "concentrate". This solution is diluted at the time of use in an injectable medium as described above for an administration by infusion. It is also possible to take up the lyophilizate in water fip and then to dilute the concentrate thus obtained in the desired injectable medium.

The frozen formulations can be frozen from solutions initially prepared, containing 5 to 250 mg/ml, or from diluted solutions, for the preparation of frozen bags, for example. The frozen formulations are thawed at the time of use and then diluted, if necessary.

The solutions presented in the liquid state contain 5 to 250 mg/ml of active principle. They are diluted at the time of use to concentrations ranging from 0.5 to 10 mg/ml.

The term additive is understood hereinabove to refer to a buffer solution chosen from any pharmaceutically acceptable aqueous solution buffered to acidic pH, capable of fixing the pH of the medium at a value below the pH of the blood plasma, and in particular at values at which the stability of the quinupristine/dalfopristine combination is not affected, i.e. at values which do not entail any immediate or rapid degradation of one and/or the other of the active principles. Preferably, the term additive is understood to refer to any pharmaceutically acceptable solution buffered to a pH ranging from 3 to 6.

Preferably, mention may be made of any pharmaceutically acceptable solution formed by an acid/base system in which at least one of the constituents is a pharmaceutically acceptable weak acid or weak base whose pKa is within the range of from 3 to 6, and in which the resultant pH of the system is in the region of or below the above pKa.

Even more preferably, the system can comprise one or more pharmaceutically acceptable weak organic or inorganic acids whose pKa is within the range from 3 to 6, combined with its conjugate base, with a strong base or with a weak base, or alternatively the system can comprise one or more pharmaceutically acceptable strong organic or inorganic acids, combined with at least one weak base belonging to an acid/base couple whose pKa is within the range from 3 to 6.

The acids given below (or their conjugate bases) are examples of acids which can form part of the composition of the system: citric acid, acetic acid, lactic acid, amino acids, malic acid, ascorbic acid, glutamic acid, benzoic acid, histidine, glutaric acid, propionic acid, succinic acid, formic acid, maleic acid, aspartic acid, malonic acid, gluconic acid, glucoheptonic acid, and phosphoric acid. These acids can be combined with their conjugate base, with the conjugate base of another weak acid or with sodium hydroxide. The conjugate bases of the acids mentioned above can also be combined, where appropriate, with methanesulphonic acid, hydrochloric acid, phosphoric acid or sulphuric acid.

Among these examples, given without any limitation being implied, the ones which are most particularly advantageous are citric acid, acetic acid, lactic acid, amino acids and/or the conjugate bases thereof.

According to the invention, the formulations of the quinupristine/dalfopristine combination, optionally reconstituted in the form of a concentrated solution (concentrate) or diluted, can be combined with a buffer solution at the time of injection. The combination can be made, indifferently, between the concentrate and the buffer solution (prediluted where necessary), before introduction into the infusion bag. The combination can also be made directly in the infusion bag, into which the buffer solution will have been introduced beforehand in order first to form a dilute buffer solution, followed by introduction of the concentrate. According to another alternative, the buffer solution can also be introduced into the bag already containing the active principle formulation. The combination can also be made using two infusion bags, one containing the active principle in the injectable medium and the other containing the dissolved buffer solution also in the injectable medium, the two bags being connected together by a Y-shaped catheter.

According to yet another alternative, the lyophilizate can be redissolved directly with a dilute buffer solution, and the mixture can then be rediluted in any compatible and pharmaceutically acceptable injectable medium, for example directly in the infusion bag, or alternatively the lyophilizate can be redissolved by direct dilution in a compatible injectable medium already containing the buffer solution, for example, directly in an infusion bag containing the buffer solution dissolved in the injectable medium.

When frozen bags already containing the dilute solution of active principle are used, the combination will be formed by introducing the buffer solution directly into the bag.

The doses of antibacterial active principle (quinupristine+dalfopristine combination) administered to patients usually range from 5 to 15 mg/kg and preferably range from 5 to 7.5 mg/kg. It will be convenient to combine concentrations of buffer solution which are suitable for exerting the buffer effect and in a limit and in a volume such that the therapeutic tolerance threshold is not exceeded. According to a preferred aspect of the invention, the molar concentrations of acid +base can range from 0.005 to 2 mol/l in a volume of from 1 to 500 ml, the pH being fixed in the range from 3 to 6, and more particularly in the range from 3.5 to 5. Preferably, the pH is fixed between 4 and 5, and more particularly is about 4. In certain cases, it may be necessary to dilute these solutions, so as to administer to the patient a dose ranging from 1 to 15 mmol.

The combined solutions of active principle and of buffer solution are sufficiently stable for extemporaneous administration by infusion. In particular they are stable, without any appreciable degradation for a period of 6 hours at a temperature of 20° C. or for a period of 24 hours at a temperature of approximately 4° C. More particularly, the term stable solution is understood to refer to a solution which shows no opalescence or appearance of particles (visual estimation or measurement of the optical density) after at least 6 hours at a temperature ranging from 25 to 30° C.

The stabilized antibacterial pharmaceutical compositions comprising the quinupristine/dalfopristine combination are prepared by simultaneous or successive dissolution of the quinupristine, dalfopristine, methanesulphonic acid or hydrochloric acid in water, followed by adjusting the pH with the range from 3.5 to 5 and/or addition of a tonicity agent and/or addition of other pharmaceutically acceptable adjuvants and, where appropriate, lyophilization and/or freezing.

The inventive compositions are more particularly prepared by dissolving the quinupristine component and subsequently the dalfopristine component in water that has been acidified with methanesulphonic acid or hydrochloric acid, followed, where appropriate, by adjusting the pH to within the range from 3.5 to 5 and/or addition of a tonicity agent and/or other pharmaceutically acceptable adjuvants. Where appropriate, they are lyophilized and/or frozen. The preparation and distribution of the solution are generally carried out between 0° C. and room temperature, preferably at low temperature. This temperature depends on the duration of the preparation and on the pH. The process is preferably performed at a temperature below 10° C. These stabilized pharmaceutical compositions are optionally sterilized, in particular by sterilizing filtration.

When the stabilized pharmaceutical compositions contain a pharmaceutically acceptable adjuvant, this adjuvant is chosen from co-solvents, stabilizers, cryoprotective agents, desiccants, fillers and tonicity agents. Without any limitation being implied, the co-solvents and the solubilizing agents are preferably chosen from polyethylene glycols (polyethylene glycols 300 and 400), propylene glycol, ethanol and surfactants such as, for example, polysorbate 80 or polyoxyethylenated derivatives (cremophors); the fillers and cryoprotective agents are preferably chosen from simple sugars, for example, glucose, mannitol, fructose or sorbitol; disaccharides, for example, sucrose, lactose, trehalose or maltose; or water-soluble polymers, for example dextrans, carboxymethylcellulose, polyvinylpyrrolidone or gelatin; the stabilizers are preferably chosen from antioxidants, etc.; the tonicity agents are preferably chosen in particular from glucose, sodium chloride, glycerol, sorbitol, mannitol, fructose or dextrans 40 and 70.

According to the invention, the buffer solutions can be prepared according to the known methods commonly used, in particular by adding sodium hydroxide to a predetermined amount of acid, until the desired pH, which ranges from 3.5 to 5, is reached, followed by adding water fip until the desired volume is reached.

These solutions may in addition contain one or more compatible and pharmaceutically acceptable adjuvants such as, for example, surface active agents. Among the surface active agents which can be used, there can be mentioned in a non-limiting manner polyoxyethylenated derivatives of oil of ricin, for example, cremophors; polyhydroxyethylated sorbitan esters, such as polysorbates, and in particular polysorbate 80; or lecithin. When such adjuvants are used in the buffer solution, these agents are introduced in such a manner that, in the final composition comprising the solution of active principle and buffer solution, they are present in a total quantity of from 1 to 25 mg per mg of the dalfopristine/quinopristine combination.

It is understood that the presentation kits for the formulation of the quinupristine/dalfopristine combination and for the additive also fall within the context of the present invention. Presentation kits of any form can be suitable, in particular, for example, presentations in the form of a twin-bottle, presentations in the form of an infusion bag containing the additive and bottle(s) containing the lyophilizate, presentations in the form of an infusion bag containing the active principle and a bottle or an ampoule containing the additive, and presentations involving one or more bottles comprising the lyophilizate and a bottle or an ampoule of the additive. Devices such as two-compartment syringes may also prove to be particularly suitable.

It is understood that the present invention can also be applied to other soluble pristinamycin derivatives, particularly to derivatives with an amino-containing chain. For example, it can also be applied to derivatives as described in European patents EP 133,097, EP 135,410, EP 191,662 and EP 248,703.

The examples which follow, which are given without any limitation being implied, show how the invention can be put into practice.

Test 1

A buffer solution was prepared from 2.55 g of citric acid monohydrate and 2.59 g of trisodium citrate dihydrate, made up to 100 ml with water fip. The solution thus prepared had a pH of 4.0 and a citric acid molarity of about 210 mmol/l.

A bottle of Synercid® (70/30 dalfopristine/quinupristine combination) was reconstituted from 550 mg of lyophilizate of the 70/30 dalfopristine/quinupristine combination, by addition of 5 ml of water fip.

1 ml of this solution was introduced into 24 ml of the buffer solution prepared above. After manual homogenization, the solution was subjected to sterilizing filtration through a filter of porosity 0.22 $\mu$m (Millipore Millex SLGV filter). The chemical stability of the solution was acceptable.

Description of the Test—Rat Tail Model

Synercid® injected intradermally into the vein of the tail of rats and observed for 10 days, caused, at a concentration of 4 mg/ml, redness and then necrosis. The redness appeared above the point of injection for 2 to 3 days and was followed by necrosis on days 4 to 6.

The haematoma, the erythema, the oedema and the necrosis were evaluated on a scale from 1 to 4[1=minimum; 2=mild; 3=moderate; 4=severe]. The overall severity was assessed with regard to the highest score observed among the 4 observations. The assessment of the tolerance was expressed by the average of the scores obtained for all the animals which had received an identical treatment.

Performing the Test and Results

The solution made up as described above was administered to the rat in the model described. The results of the study show that all of the side reactions (redness, necrosis and tail loss) were eliminated when compared with the control rats which had received the same dose of Synercid® in a 5% glucose solution.

| Treatment | Day 1 | Day 2 | Day 3 | Day 4 | Day 5 | Day 6 | Day 7 | Day 8 |
|---|---|---|---|---|---|---|---|---|
| Synercid ® /5% glucose | 0.0 (6) | 2.0 (5) | 2.5 (4) | 3.7 (4) | 3.7 (4) | 3.7 (4) | 3.7 (4) | 3.7 (3) |
| Synercid ® /citrate buffer 210 mmol/l | 0.0 (6) | 0.0 (5) | 0.0 (5) | 2.0 (5) | 2.0 (5) | 0.0 (5) | 0.0 (5) | 0.0 (5) |

( ) number of surviving animals

The dalfopristine/quinupristine lyophilizate was prepared in the following way:

One liter of a solution containing 125 mg/ml of quinupristine/dalfopristine (30/70), salified with methanesulphonic acid (z 16.7 mg/ml) to a pH of 4.75, was prepared by introducing 810 g of water for injectable preparation into a dissolution tank equipped with a refrigeration unit. The solution was refrigerated to a temperature that ranged from 0 to 6° C. throughout the manufacture. 16.4 g of methanesulphonic acid were added, followed by successive introduction of 37.5 g of quinupristine, dissolved by mechanical stirring, and 87.5 g of dalfopristine, also dissolved by mechanical stirring. The pH of the solution was adjusted to 4.75 with 1N methanesulphonic acid solution. The solution was made up to 1 liter (1030 g) with water for injectable preparation.

This solution was sterilized by sterilizing filtration (0.22 μm filter), distributed into bottles [500 mg of quinupristine/dalfopristine (30/70) per bottle] and then lyophilized [freezing: temperature −30° C. to −50° C.; freezing rate about 0.5°/min. Sublimation: pressure 0.5 mbar. Secondary desiccation: pressure (≈30 μbar) temperature 40° C.].

Tests 2 to 5

Working as in Test 1 and diluting the buffer solution with a 5% glucose solution, the following results were obtained:

| Treatment | Day 1 | Day 2 | Day 3 | Day 4 | Day 5 | Day 6 | Day 7 | Day 8 |
|---|---|---|---|---|---|---|---|---|
| Synercid ® /5% glucose | 0.5 (6) | 1.8 (5) | 2.4 (5) | 2.8 (5) | 2.6 (5) | 2.6 (5) | 2.6 (5) | 2.4 (5) |
| Synercid ® /citrate buffer 50 mmol/l | 0.2 (6) | 0.5 (6) | 0.3 (6) | 0.5 (6) | 0.3 (6) | 2.0 (6) | 0.0 (6) | 0.0 (6) |
| Synercid ® /citrate buffer 25 mmol/l | 0.2 (6) | 0.8 (6) | 0.5 (6) | 0.3 (6) | 0.3 (6) | 0.2 (6) | 0.2 (6) | 0.0 (6) |
| Synercid ® /citrate buffer 12.5 mmol/l | 0.5 (6) | 0.8 (6) | 0.5 (6) | 0.5 (6) | 0.3 (6) | 0.2 (6) | 0.2 (6) | 0.2 (6) |
| Synercid ® /citrate buffer 6.25 mmol/l | 0.2 (6) | 0.2 (6) | 0.3 (6) | 0.3 (6) | 0.3 (6) | 0.2 (6) | 0.0 (6) | 0.0 (6) |

( ) number of surviving animals

The results of the study show that all of the side reactions (redness, necrosis and tail loss) were eliminated or greatly reduced compared with the control rats which received the same dose of Synercid® in a 5% glucose solution.

Test 6

A test identical to Test 1 described above was carried out, preparing a buffer solution containing 0.35 ml of 99% acetic acid, 1.92 g of sodium acetate trihydrate and 0.19 g of sodium chloride, made up to 100 ml with water fip. The solution thus prepared had a pH of 5.02.

After sterilizing filtration of the solution as described above, the chemical stability of the solution was acceptable.

Test 7: Clinical Study

The dose of 7.5 mg/kg of Synercid® (70/30 dalfopristine/quinupristine combination) taken up for 1 hour in a volume of 250 ml of aqueous 5% glucose solution corresponds to the unit dose used clinically via the i.v. route.

An acidic citrate buffer solution at 20 mM/l was prepared (5 mM in a solution o& 250 ml containing 1051 mg of citric acid monohydrate).

A treatment of 48 hours was usually sufficient for the venous intolerance reactions to appear.

8 individuals per group were selected. The criteria for stopping the treatment were defined beforehand, based on significant pain, induration of the vein or the decision of the patient or of the investigator to stop the treatment.

After treatment for 2 days, pains were experienced and erythema observed at the site of injection, but no phenomenon of venous thrombosis appeared and no interruption of the treatment was necessary. The conclusion of the test, in accordance with the defined procedure, is a marked improvement in the general tolerance to this concentration of citrate buffer.

What is claimed is:

1. An injectable composition, said composition comprising an aqueous solution of dalfopristine and quinupristine, and an additive effective to avoid or reduce intolerance effects at the site of injection.

2. An injectable composition according to claim 1, wherein said additive is a buffer solution.

3. An injectable composition according to claim 1, wherein said additive is a pharmaceutically acceptable aqueous solution buffered to acidic pH, is capable of fixing the pH of the composition at a value below the pH of the blood plasma, and is capable of fixing the pH of the composition at a value at which the stability of the dalfopristine and quinupristine compounds is not affected.

4. An injectable composition according to claim 1, wherein said additive is a pharmaceutically acceptable solution buffered to a pH ranging from 3 to 6.

5. An injectable composition according to claim 1, wherein said additive is a pharmaceutically acceptable solution formed by an acid/base system in which at least one component is a pharmaceutically acceptable weak acid or weak base whose pKa ranges from 3 to 6, and in which the resultant pH of the acid/base system is in the range of or below said pKa.

6. An injectable composition according to claim 2, wherein the pH of said buffer solution is fixed at a value ranging from 3.5 to 5.

7. An injectable composition according to claim 6, wherein the pH of said buffer solution is fixed at a value ranging from 4 to 5.

8. An injectable composition according to claim 7, wherein the pH of said buffer solution is fixed at a value of about 4.

9. An injectable composition according to claim 1, wherein said additive is a pharmaceutically acceptable buffer solution formed by combining
   an acid/base system comprising one or more pharmaceutically acceptable weak organic or inorganic acids whose pKa ranges from 3 to 6, with its conjugate base, with a strong base, or with a weak base differing from said conjugate base, or
   an acid/base system comprising one or more pharmaceutically acceptable strong organic or inorganic acids with at least one weak base belonging to an acid/base couple whose pKa ranges from 3 to 6.

10. An injectable composition according to claim 9, wherein said acid/base system comprises an acid or its conjugate base, said acid being citric acid, acetic acid, lactic acid, an amino acid, malic acid, ascorbic acid, glutamic acid, benzoic acid, histidine, glutaric acid, propionic acid, succinic acid, formic acid, maleic acid, aspartic acid, malonic acid, gluconic acid, glucoheptonic acid, or phosphoric acid, wherein said acid is associated with its conjugate base, with the conjugate base of another weak acid or with sodium hydroxide, and wherein said conjugate base of any of said acids is combined with methanesulphonic acid, hydrochloric acid, phosphoric acid or sulphuric acid.

11. An injectable composition according to claim 10, wherein said acid/base system comprises citric acid, acetic acid, lactic acid, or an amino acid, or comprises a conjugate base of citric acid, acetic acid, lactic acid, or of an amino acid.

12. An injectable composition according to claim 2, wherein said buffered solution further contains a surface-active agent.

13. An injectable composition according to claim 12, wherein said surface-active agent is a polyoxyethylenated castor oil derivative, an ester of polyhydroxyethyl sorbitan, or a lecithin.

14. An injectable composition according to claim 13, wherein said surface-active agent is polysorbate 80.

15. A twin-compartment for preparing a solution for injection, said twin-compartment comprising a first compartment containing an aqueous solution of dalfopristine and quinupristine, and a second compartment containing an additive effective to avoid or reduce intolerance effects at the site of injection.

16. An injectable composition according to claim 1, wherein said aqueous solution of dalfopristine and quinupristine comprises methanesulphonic acid or hydrochloric acid in at least a stoichiometric amount relative to the total amount of dalfopristine and quinupristine present in said aqueous solution, and wherein the pH of said aqueous solution ranges from 3.5 to 5.

17. A method for protecting against venous intolerance effects caused by the injection of a composition containing quinupristine and dalfopristine, said method comprising adding to said composition prior to injection a buffer solution selected from any pharmaceutically acceptable aqueous solution that is buffered to an acid pH, that is capable of fixing the pH of the composition at a value below the pH of blood plasma, and that is capable of fixing the pH of the composition at a value that does not cause immediate or rapid degradation of the quinupristine, dalfopristine, or any other active component in the composition.

18. A method according to claim 17, wherein said buffer solution is a pharmaceutically acceptable solution buffered to a pH ranging from 3 to 6.

19. A method according to claim 17, wherein said buffer solution is a pharmaceutically acceptable solution formed by an acid/base system in which at least one component is a pharmaceutically acceptable weak acid or weak base whose pKa ranges from 3 to 6, and in which the resultant pH of the acid/base system is in the range of or below said pKa.

20. A method according to claim 17, wherein said buffer solution is formed by combining
   an acid/base system comprising one or more pharmaceutically acceptable weak organic or inorganic acids whose pKa ranges from 3 to 6, with its conjugate base, with a strong base, or with a weak base differing from said conjugate base, or
   an acid/base system comprising one or more pharmaceutically acceptable strong organic or inorganic acids with at least one weak base belonging to an acid/base couple whose pKa ranges from 3 to 6.

21. A method according to claim 20, wherein said buffer solution is formed by an acid/base system comprising an acid or its conjugate base, said acid being citric acid, acetic acid, lactic acid, an amino acid, malic acid, ascorbic acid, glutamic acid, benzoic acid, histidine, glutaric acid, propionic acid, succinic acid, formic acid, maleic acid, aspartic acid, malonic acid, gluconic acid, glucoheptonic acid, or phosphoric acid, wherein said acid is associated with its conjugate base, with the conjugate base of another weak acid or with sodium hydroxide, and wherein said conjugate base of any of said acids is combined with methanesulphonic acid, hydrochloric acid, phosphoric acid or sulphuric acid.

22. A method according to claim 17, wherein said buffered solution further contains a surface-active agent.

23. A method according to claim 22, wherein said surface-active agent is a polyoxyethylenated castor oil derivative, an ester of polyhydroxyethyl sorbitan, or a lecithin.

24. A method according to claim 23, wherein said surface-active agent is polysorbate 80.

25. A kit, said kit comprising a first compartment containing an injectable composition comprising an aqueous solution of dalfopristine and quinupristine, and a second compartment containing an additive effective to avoid or reduce intolerance effects at the site of injection.

26. A kit according to claim 25, wherein said additive is a buffer solution.

27. A kit according to claim 26, wherein said buffer solution is a pharmaceutically acceptable solution that is buffered to acidic pH, that is capable of fixing the pH of said injectable composition at a value below the pH of the blood plasma, and that is capable of fixing the pH of said injectable composition at a value at which the stability of the dalfopristine and quinupristine compounds is not affected.

28. A kit according to claim 25, further comprising methanesulphonic acid or hydrochloric acid, wherein said methanesulphonic acid or hydrochloric acid is added in at least a stoichiometric amount relative to the total amount of dalfopristine and quinupristine present in said injectable composition and wherein the pH of said composition ranges from 3.5 to 5.

29. A kit according to claim 25, said kit comprising a twin-bottle, an infusion bag containing said additive and at least one bottle containing a lyophilized formulation of quinupristine and dalfopristine, an infusion bag containing quinupristine and dalfopristine and a bottle or an ampoule containing said additive, at least one bottle containing a lyophilized formulation of quinupristine and dalfopristine and a bottle or an ampoule containing said additive, or a two-compartment syringe.

30. A method for treating a bacterial infection, said method comprising injecting into a patient an injectable composition according to claim 1 comprising an aqueous solution of dalfopristine and quinupristine, and an additive effective to avoid or reduce intolerance effects at the site of injection.

31. A method according to claim 30, wherein said bacterial infection is caused by a vancomycin-resistant microorganism.

32. A method according to claim 30, wherein said additive is a pharmaceutically acceptable aqueous solution buffered to acidic pH, is capable of fixing the pH of the composition at a value below the pH of the blood plasma, and is capable of fixing the pH of the composition at a value at which the stability of the dalfopristine and quinupristine compounds is not affected.

33. A method according to claim 32, wherein said additive is a pharmaceutically acceptable solution buffered to a pH ranging from 3 to 6.

34. A method according to claim 33, wherein said additive is a pharmaceutically acceptable solution formed by an acid/base system in which at least one component is a pharmaceutically acceptable weak acid or weak base whose pKa ranges from 3 to 6, and in which the resultant pH of the acid/base system is in the range of or below said pKa.

35. A method according to claim 30, wherein said dalfopristine and quinupristine are present in said injectable composition in an amount such that from 5 to 15 mg/kg thereof are injected into said patient.

36. A method according to claim 35, wherein said dalfopristine and quinupristine are present in said injectable composition in an amount such that from 5 to 7.5 mg/kg thereof are injected into said patient.

37. An injectable composition according to claim 1, which composition does not experience any visually appreciable degradation for a period of 6 hours at a temperature of 20° C.

38. An injectable composition according to claim 1, which composition does not experience any appreciable degradation for a period of 24 hours at a temperature of approximately 4° C.

39. An injectable composition according to claim 1, which composition shows no opalescence or appearance of particles after at least 6 hours at a temperature ranging from 250 to 30° C.

40. An injectable composition according to claim 4, wherein said buffer solution comprises citric acid monohydrate.

41. An injectable composition according to claim 4, wherein said buffer solution comprises citric acid monohydrate and trisodium citrate dihydrate.

42. An injectable composition according to claim 4, wherein said buffer solution comprises acetic acid, sodium acetate trihydrate and sodium chloride.

43. An injectable composition according to claim 16, further comprising methanesulphonic acid in at least a stoichiometric amount relative to the total amount of dalfopristine and quinupristine present in said composition.

44. A method for buffering an injectable composition comprising dalfopristine and quinupristine, said method comprising including in said injectable composition a pharmaceutically acceptable aqueous solution that is buffered to acidic pH, that is capable of fixing the pH of the composition at a value below the pH of the blood plasma, and that is capable of fixing the pH of the composition at a value at which the stability of the dalfopristine and quinupristine compounds is not affected, wherein said buffered aqueous solution protects the site of injection against venous intolerance effects caused by injection of a composition containing dalfopristine and quinupristine, and wherein the buffered injectable composition is an injectable composition according to claim 3.

45. A method according to claim 44, wherein said aqueous solution is buffered to a pH in the range of from 3 to 6.

46. A method according to claim 44, wherein said aqueous solution is a pharmaceutically acceptable solution formed by an acid/base system in which at least one component is a pharmaceutically acceptable weak acid or weak base whose pKa ranges from 3 to 6, and in which the resultant pH of the acid/base system is in the range of or below said pKa.

* * * * *